(12) United States Patent
Wilson et al.

(10) Patent No.: US 6,409,655 B1
(45) Date of Patent: *Jun. 25, 2002

(54) DEVICE FOR APPLYING STIMULI TO A SUBJECT

(76) Inventors: David L. Wilson, 616 Azalea Ave., Redding, CA (US) 96002; Douglas C. Fisher, 5151 Ward Rd., #3, Wheatridge, CO (US) 80033

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/263,116

(22) Filed: Mar. 5, 1999

(51) Int. Cl.$^7$ ............................................. A61M 21/00
(52) U.S. Cl. ...................................................... 600/28
(58) Field of Search ............................ 600/26, 17, 28; 128/908; 351/203

(56) References Cited

U.S. PATENT DOCUMENTS

| | | | | |
|---|---|---|---|---|
| 5,219,322 A | * | 6/1993 | Weathers | 600/27 |
| 5,304,112 A | * | 4/1994 | Mrklas et al. | 600/27 |
| 5,343,261 A | | 8/1994 | Wilson | |
| 5,725,472 A | * | 3/1998 | Weathers | 600/27 X |
| 6,090,037 A | * | 7/2000 | Gavish | 600/27 |

* cited by examiner

Primary Examiner—John P. Lacyk
Assistant Examiner—Joseph A Cadugan
(74) Attorney, Agent, or Firm—Theodore J. Bielen, Jr.

(57) ABSTRACT

A device for applying stimuli to a subject for therapeutic purposes utilizing an audio source producing a selected audio tone. An audio speaker delivers the audio stimulus to the left and right ears of the subject in an alternating manner, such that the sounds may be heard in either of the ears or may be heard in both of the ears in sequential fashion. Visual or tactile stimuli may be delivered to a subject singularly or simultaneously with the audio stimulus.

8 Claims, 3 Drawing Sheets

DEVICE FOR APPLYING STIMULI TO A SUBJECT

BACKGROUND OF THE INVENTION

It is known that Post-Traumatic Stress Disorder (PTSD) may be treated by providing a particular type of desensitization, known as eye movement desensitization reprocessing (EMDR). Early treatments centered on desensitization of eye movements.

Reference is made to U.S. Pat. No. 5,343,261 to Wilson which revealed a novel device based on a treatment process first reported in an article entitled "Eye Movement Desensitization: A New Treatment For Post-Traumatic Stress Disorder" by F. Shapiro. In fact, the device for providing desensitizing eye movements described in this document has been successfully employed in the treatment of PTSD.

It has been proposed that other sensory stimuli may be utilized in a rhythmic manner to achieve the same effect. For example, the application of alternating auditory stimuli and/or tactile stimuli have achieved good results in the treatment of PTSD and many other emotional disorders.

A device which is capable of applying multiple stimuli, be it auditory, visual, or tactile, to a subject in a coordinated fashion would be a notable advance in the psychological treatment field.

SUMMARY OF THE INVENTION

In accordance with the present invention a novel and useful device for applying multiple stimuli to a subject for the treatment of trauma is herein provided.

The device of the present invention utilizes an audio source which provides a selected audio tone. Such audio tones may be internally generated or provided from an external source. The audio tones may be fed to audio speaker means, which may be in the form of a set of head phones. Each audio tone received may be adjusted as to volume and speed. The audio speaker means may also deliver selected audio tones to the left and right ears of the subject in a discrete alternate manner. Such alternation may also include the sequence of all sound being delivered to the left ear, all sound being delivered to the left and rights ears, and all sound being delivered to the right ear of the listener or patient. In this bridging manner, there is no time period in which sound is not being delivered to one of the ears of the listener. The audio tones may comprise pure notes or more complicated sonic patterns. Also, narratives such as, relaxation sounds, affirmations, prayers, and the like, may be delivered bilaterally or alternately to a patient's ears. In addition, switch means may be provided for selecting either the internally generated audio source or an external audio source, according to the needs of the patient. Further, internally generated tones may consist of a single tone of varying pitch or successive tones on a scale, e.g. a scale of eight notes (CDEFGABC).

Means may also be found in the present invention for providing a tactile output to the patient commensurate with the alternating delivery of the audio tones. Such tactile delivery may take the form of a tactile probe which is graspable by the user and is activated by an electrical signal which initiates vibration of the probe. The probe vibration is generated by conventional motors, solenoids or similar devices, which may be found within a housing or tubing.

Although the device of the present invention may be manually applied or started, initiation may derive from other sources. For example, means may be included for quantifying a variable body characteristic. Such body characteristics may take the form of the patient's pulse, body temperature, blood pressure galvanic skin response (GSR), eye blink rate, and the like. The particular body characteristic is quantified and averaged. An indicator is employed to measure the rate of change of the variable body characteristic. When such rate of change exceeds a certain predetermined amount, the delivery of selected audio tones may be altered accordingly. For example, a change in pulse rate may change the pitch of the tones being delivered alternatively to the ears of the user, may switch from an internally generated tones to an external audio source, from auditory stimuli to tactile and/or visual stimuli, and the like. Of course, such alternation characteristics of any sensory input may be preselected by the operator of the system of the present invention.

The audio and tactile portion of the system of the present invention may be used in conjunction with visual scanning devices such as that found in U.S. Pat. No. 5,343,261 and our U.S. Pat. No. 6,056,403, which is incorporated by reference in its entirety to this application. That is to say, alternating tones may be coordinated with alternating visual signals of varying types.

It may be apparent that a novel and useful device for applying stimuli to a subject for the purpose of therapy has been hereinabove described.

It is therefore an object of the present invention to provide a device for applying therapeutic stimuli to a subject which employs multiple single sensory mode stimuli in a coordinated fashion.

Another object of the present invention is to provide a device for applying therapeutic stimuli to a subject which utilizes audio tones which are alternatively delivered to the left and rights ears of a subject.

Another object of the present invention is to provide a device for applying therapeutic stimuli to a subject which employs audio signals and tones that are delivered alternatively to the left and right ears of the subject and is triggered by a variable body characteristic, such as body temperature, the galvanic skin response, blood pressure, pulse rate, and the like.

Yet another object of the present invention is to provide a device for applying therapeutic stimuli to a subject which is useful as a desensitization apparatus, and, thus serves as a tool in psychological treatment.

Another object of the present invention is to provide a device for applying therapeutic stimuli to a subject which may be employed to treat an individual or a plurality of persons simultaneously, for example, in psychotherapy with couples.

A further object of the present invention is to provide a device for applying therapeutic stimuli to a subject which delivers multiple stimuli to a patient or patients and is manually adjustable, preprogrammed, or triggered by physiological events.

Another object of the present invention is to provide a device for applying therapeutic stimuli to a subject which is modular in nature and may be upgraded or downgraded commensurate with features desired by the therapist employing such a device.

Another object of the present invention is to provide a device for applying therapeutic stimuli which employs audio sources that are internally generated or found externally to the system.

Yet another object of the present invention is to provide a device for applying therapeutic stimuli to a subject which uses an audio signal that is directed individually and simultaneously to the ears of the patient in a sequential fashion.

A further object of the present invention is to provide a device for applying a variety of audio therapeutic stimuli to the ears of a subject or subjects in a alternating or bilateral fashion, such as tones, music, relaxation sounds, affirmations, prayers, and the like.

The invention possesses other objects and advantages especially as concerns particular characteristics and features thereof which will become apparent as the specification continues.

For a better understanding of the invention reference is made to the following detailed description of the preferred embodiments thereof which should be taken in conjunction with the prior described drawings.

DETAILED DESCRIPTION OF THE PREFERRED EMBODIMENTS

Various aspects of the present invention will evolve from the following detailed description of the device of the present invention which must be referenced to the accompanying drawings to achieve a full understanding of the invention.

Figure 1:
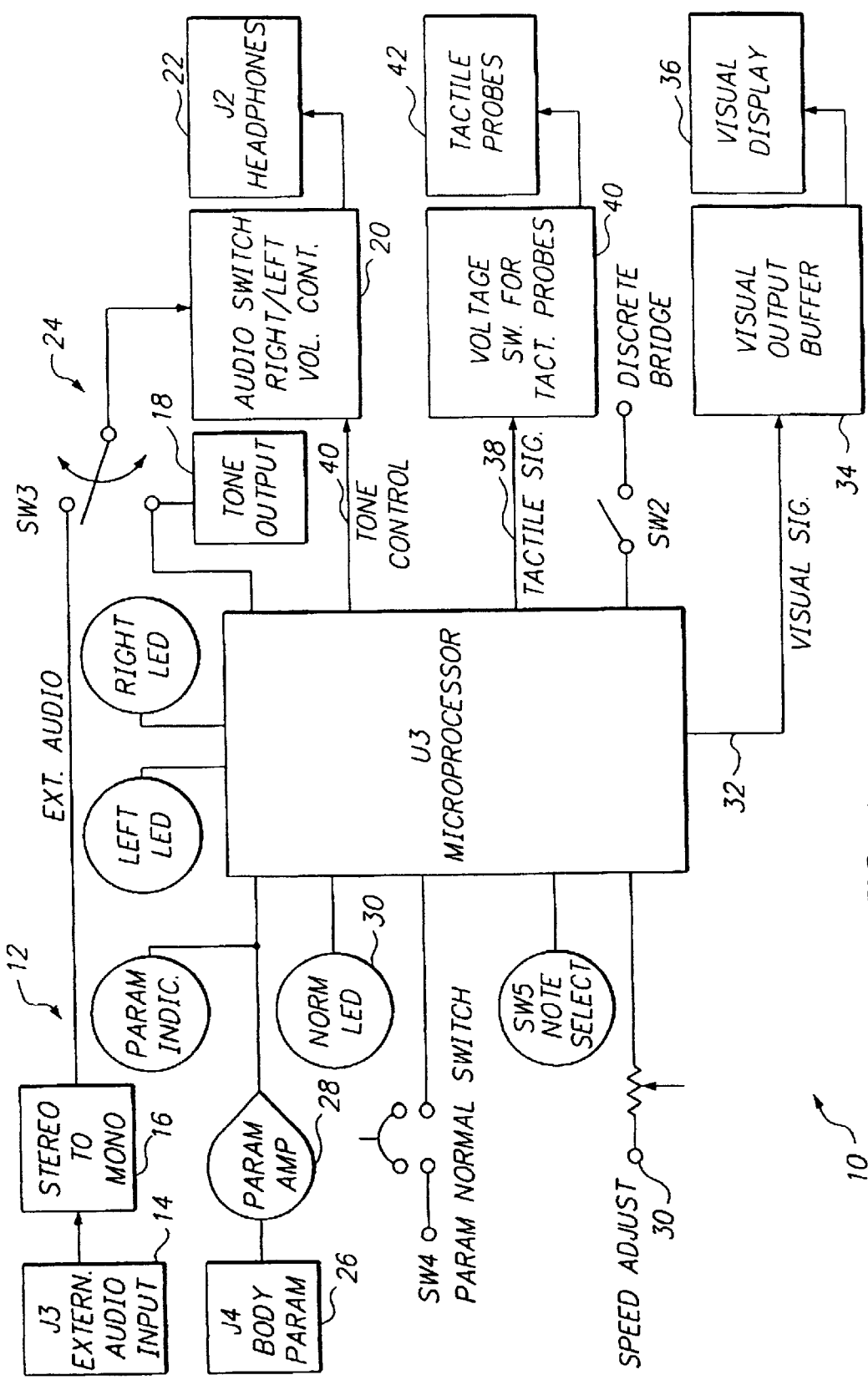
FIG. 1 is a block diagram describing in detail the operation of the device of the present invention.

The invention as a whole is shown in the drawings by reference character 10. Device 10 includes as one of its elements a microprocessor U3, FIG. 1. Microprocessor U3 may be of the type with the designation 68HC705. Microprocessor U3 serves to direct and to coordinate multiple inputs and outputs in the system 10 of the present invention. The programmed binary code for U3 is attached hereto as Appendix I. For example, audio source 12 an external audio input 14, such as a tape recorder, CD drive, and the like to stereo to monaural converter 16. Audio source 12 may also take the form of internal audio source 18 which is capable of generating a single tone or a multiplicity of tones. For example, eight notes of a scale (CDEFGABC) may be employed in this regard. Switch means SW3 permits the user of device 10 to select internal tone generator 18 or external audio input 14 into audio switch 20. Internal tone generator 18, separately depicted, originates in microprocessor U3. Tone control output 40 from U3 passes to right/left volume control and audio switch 20. The output of audio switch 20 passes to J2 headphones 22 which are worn by the user or patient being treated by the clinician who operates device 10. Headphones 22 may receive a continuous tone alternated from the left side to the right side of the headphones. In the bridge mode, the external audio source 14 is heard by the user or patient wearing headphones 22, first in the right ear, followed by both the left and right ears, and, finally, the left ear from the corresponding sides of headphones 22. Thus, in the bridge mode there is never a time that one side or the other of headphones 22 is not switched on. A discrete mode may also be employed, through right/left volume control 20, in which a tone is heard momentarily in each ear through headphones 22 in this case. Thus, in the discrete mode, there is a period of time when neither the left or right portions of headphones 22 is switched on. Thus, these elements comprise means 24 for delivering selected audio tones to the left and right ears of the subject. Switch SW5 is capable of selecting a particular note to be fed into microprocessor U3 for use in headphones 22. In addition adjustment 30 is capable of varying the periodicity of a particular note. It should be apparent that the audio signal to headphones 22 may be split for use in multiple headsets.

Means 26 is also depicted for quantifying a variable body characteristic of the subject or patient. Such means 26 is labeled as J4 body param on FIG. 1. Means 26 may acquire the pulse rate, body temperature, blood pressure, eye blink rate, galvanic skin response (GSR), and the like from the patient. Such signal is sent to the parameter amplifier 28 and then to microprocessor U3. For example, means 26 may acquire the pulse from the patient through a finger clip, ear clip, or a similar type device of conventional configuration. A gain adjustment allows a weak signal from means 26 to successfully be inputted to microprocessor U3. After a time period, microprocessor U3 calculates an average pulse rate and turns on normalized LED 31 so that the particular parameter of the patient may now be used as a reference. The operator or clinician pushes SW4, the parameter normalized switch. The connecting of switch SW4 will cause the audio switch 20 to select a particular tone to be sent to audio speaker means 22 in the form of headphones. In this mode, SW3 would be set to internal tone source 18. U3 may be programmed to automatically change tones sent from internal output 18 to headphones 22, dependent on the level fed to microprocessor U3 via parameter output 28.

Further, microprocessor U3 may send a visual signal through leg 32 to visual output buffer 34 which is then passed to visual display 36. Visual display 36 may take the form of a light bar, light panel, light goggles, and the like described in U.S. Pat. No. 5,343,261. Microprocessor U3 is able to coordinate periodic tones to headphones 22 with visual signals passing through leg 32 to visual display 36.

Moreover, a tactile signal 38 leaves microprocessor U3 and pass to a plurality of voltages switches 40 for a tactile probe or probes 42. Tactile probe 42 may simply take the form of a vibrator that is intended to be held by the hands or pressed against the skin of the patient. Again, the tactile signal 38 may be coordinated with the tone output through leg 40 and the visual signal through leg 32. Thus, any stimuli, sonic, tactile, or visual, are acquired by the patient alone or in combination.

Figure 2:
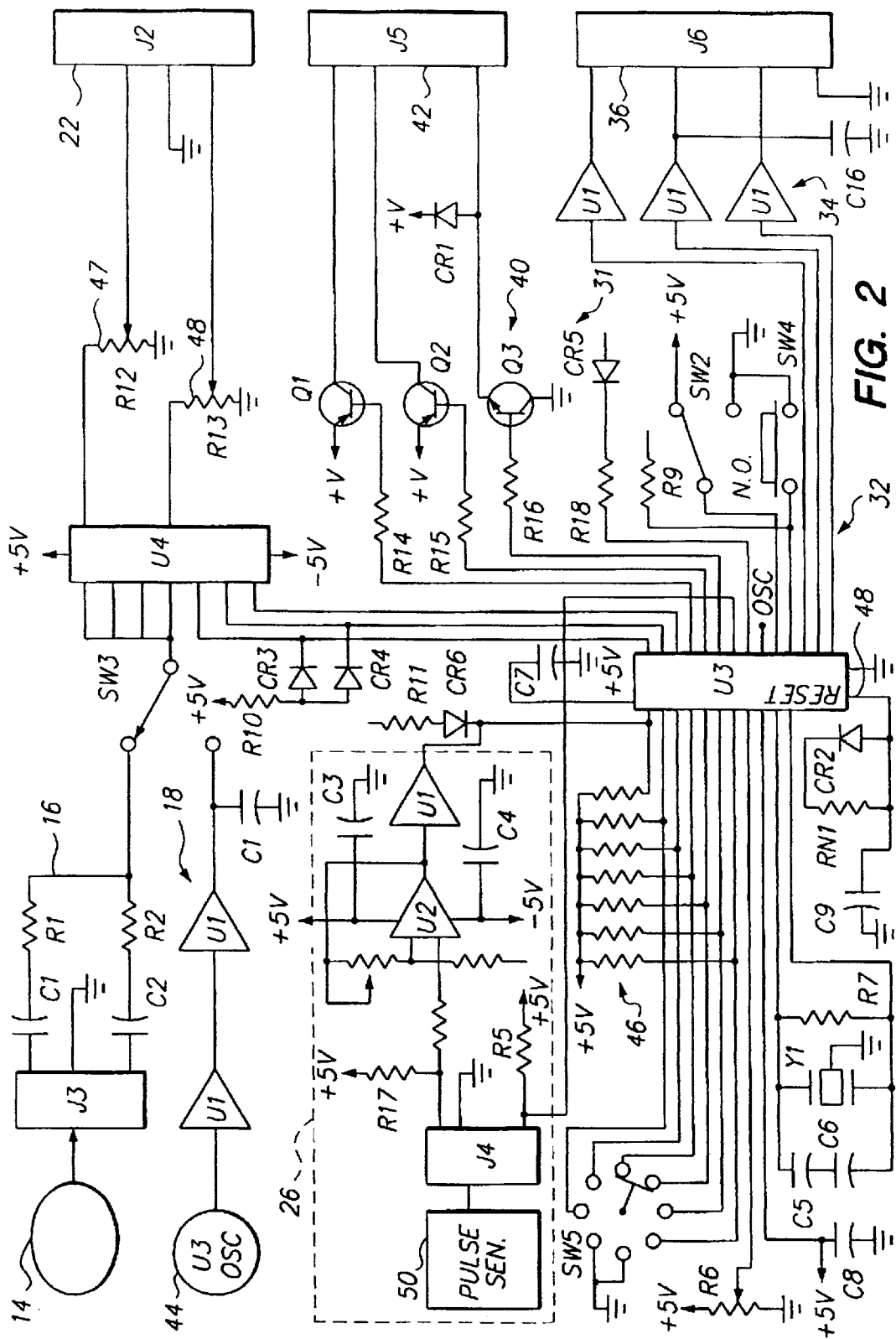
FIG. 2 is a schematic block diagram detailing the electrical interaction of the electrical components of the present application.

With reference to FIG. 2, it may be observed that the particular circuitry used in the present invention is shown. J3 represents the connector plug for the external audio source. Capacitors C1 and C2, in conjunction with resistors R1 and R2, comprise the stereo-to-monaural 16 converter. The monaural signal passes through leg 42 to switch SW3 which determines the source of the audio output from U3. U3 oscillator 44 passes through Schmidt trigger U1. Capacitor C1 acts as a filter. Oscillator 44 is capable of generating internal tones either singularly or along a scale. U4 serves as a multiplexor and receives three signals from U3. Multiplexor U4 feeds headphones 22 (J2) having a right volume control 46 and a left volume control 48. Switch SW5 determines one of eight internally generated tones, deriving from oscillator 44, sent to microprocessor U3. Resistor R6 regulates the rate of alternation of tones between the left and right sides of headphones 22, and is essentially an analog-to-digital converter. Thus, R6 controls the rate of switching of the multiplex tones traveling from left to right in headset 22. Resistors 47 modulate the signals from SW5 and are considered to be pull-up resistors. SW2, controlled by the clinician, determines the "bridge mode" or "discrete mode" for tones emanating from internal tone output 18.

Oscillator Y1 is a reference oscillator and produces a time base used by microprocessor U3. Oscillator Y1 acts in conjunction with C5, C6, C8, and R7 in this regard. U3 generates a reset pulse to reset pin 48. Following the charging of C9, the reset function of U3 is turned off.

Turning to CR3 and CR4, such diodes serve as visual indicators to the right side and left side of headphone 22, respectively. Thus, the clinician is able to instantly perceive which part of headset 22 is activated when used by the patient R10 serves as a current limiter.

Referring to means 26, a human parameter or physiological characteristic, such as pulse rate, GSR, temperature, and the like, is quantified. J4 serves as the input and CR5 serves as an indicator 31, FIG. 2, of the same when a normalized parameter has been achieved. As prior explained, this is performed through an averaging of, say pulse rate, over a period of time by U3. U2 serves as an amplifier for the signal generated by pulse sensor 50. U1 produces a square wave signal of a digital nature, the output of which is fed into microprocessor U3. CR6 indicates the input to U2. The power input to system 10 on FIG. 2 is indicated at various areas by a number followed by the letter "V". For example, plus 5 volts and minus 5 volts are fed into operational amplifier U2.

J5 represents a tactile probe or probes 42 and is driven by a voltage, +V at transistors Q1, Q2, and Q3. In certain cases, the voltage, +V is at or about 9 volts. Again, microprocessor U3 generates a signal to operate transistor switches Q1, Q2, and Q3 to activate tactile probes 42. CR1 is a back EMF suppression diode which protects Q1, Q2, and Q3 from inductive kickback from conventional motors employed with tactile probes 42.

SW4 is the parameter normalized switch that permits the clinician to begin the body parameter input to U3 when such body parameter has been normalized. In other words, when the patients pulse rate reaches a normal level, SW4 is pushed.

Again, when the body parameter, i.e. Pulse enters J5, tones may be initiated in headphones J2 through microprocessor U3. A rise in pulse from the average pulse determined at SW4 is able to switch tones at SW5 in a sequential fashion. For example, a rise in pulse may produce a tone which is higher or lower than the prior tone fed to headphones J2, and vice versa. In this regard, the "discrete bridge" function is operated through SW2. That is to say, internal tones generated by oscillator 44 and U1, by the selection through SW3, will alternately travel to the left ear, both the left and right ears, and the right ear of the patient in this sequence. Switching SW2 brings in the "discrete mode" in which the sound is passed to headphones J2 alternately, left and right without both ear phones 54 or 56 (FIG. 3) being activated. In other words, a sound gap exists between the alternating left and right sounds received by the patient's ears.

J6 represents the optional visual output portion of device 10 in which a light bar, such as that shown in U.S. Pat. No. 5,343,261 may be employed and be coordinated with the alternating tones passing to headphones J2, as well as tactile probes at J5.

The following is a table representing typical components used in the circuitry found in FIG. 2.

TABLE OF COMPONENTS

| Component | Value or Identification |
|---|---|
| C1 | 0.1 F |
| C2 | 0.1 F |
| C3 | 0.1 F |
| C4 | 10 µF |
| C5 | 47 pF |
| C6 | 47 pF |
| C7 | 0.1 F |
| C8 | 0.1 F |
| C9 | 10 µF |
| C14 | 10 µF |
| C15 | 100 µF |
| C16 | 0.1 F |
| R1 | 180 Ω |
| R2 | 180 Ω |
| R3 | 10K Ω |
| R4 | 10K Ω |
| R5 | 390 Ω |
| R6 | 10K Ω |
| R7 | 10M Ω |
| R9 | 10K Ω |
| R10 | 390 Ω |
| R11 | 1K Ω |
| R12 | 20K Ω |
| R13 | 20K Ω |
| R14 | 1K Ω |
| R15 | 1K Ω |
| R16 | 1K Ω |
| R17 | 390 Ω |
| R18 | 390 Ω |
| RN1 | 10K Ω |
| U1 | 74HCT14 |
| U2 | LT1097 |
| U3 | 68HC705 |
| U4 | 4052 |
| Q1 | 2N3906 |
| Q2 | 2N3906 |
| Q3 | 2N3904 |
| CR2–CR6 | 1N914 |

Figure 3:
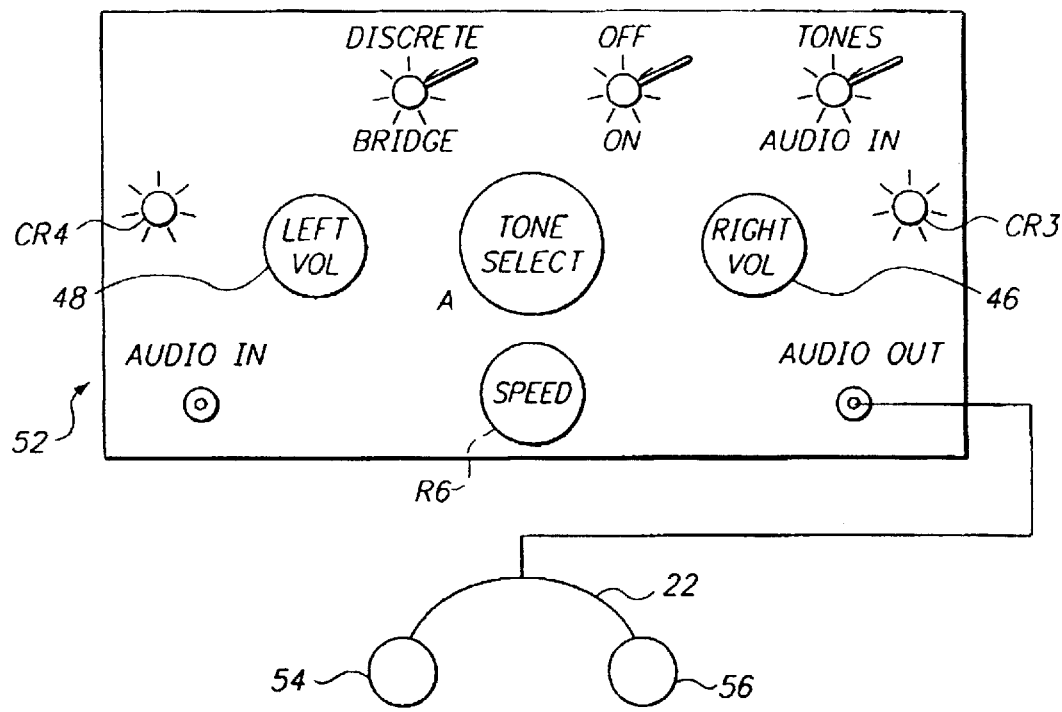
FIG. 3 is a schematic front view of the panel of the audio scanning portion of the present invention.
Figure 4:
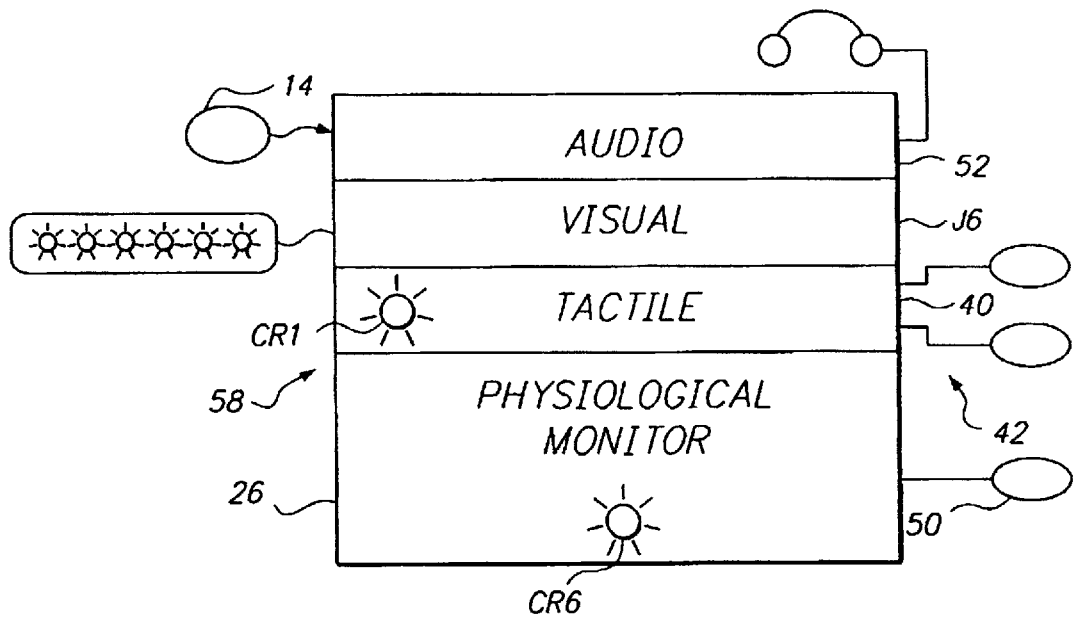
FIG. 4 is a front view of stacked components, of the present invention.

FIGS. 3 and 4 show a housing 52 permitting the clinician to operate device 10. Headset 22 is depicted schematically having left earpiece 54 and right earpiece 56.

FIG. 4 indicates that an external audio source 14 may be jacked into audio portion 52 shown in FIG. 3. Other components 58, such as the visual component J6, the tactile component J5, the parameter sensor 26, and the like may be stacked in a modular way. That is to say, portions of system 10, of the present invention, may be used alone or in combination as desired by the clinician.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A device for applying therapeutic stimuli to a subject, comprising:
   a. means for generating a selected audio tone signal;
   b. audio speaker means transducing said audio tone signal into a selected audio tone and continuously delivering said selected audio tone to the left and right ears of the subject, said audio speaker means sequentially delivering of said audio tone to the subject's left ear, both the left and right ears, and the right ear of the listener, without interruption of said audio tone.

2. The device of claim 1 in which said selected audio tone derives from a musical scale.

3. The device of claim 1 in which said audio speaker means is a headphone.

4. The device of claim 1 which additionally comprises means for quantifying a variable body characteristic of the subject and producing a body characteristic signal, and said audio source further includes means for providing a plurality of audio tones and means for selecting one of said audio tones dependent on said quantified variable body characteristic.

5. The device of claim 1 which additionally comprises means for providing a visual display commensurate with said alternating delivery of said audio tone.

6. The device of claim 1 which further comprises a tactile output commensurate with said alternating delivery of said audio tone.

7. The device of claim 6 which additionally comprises means for providing a visual display commensurate with said alternating delivery of said audio tone.

8. The device of claim 1 which further comprises speed adjusting means for determining the time interval between said alternating of said audio tone between the left ear and right ear.

* * * * *